(12) United States Patent
He et al.

(10) Patent No.: US 12,366,582 B2
(45) Date of Patent: Jul. 22, 2025

(54) COLLAGEN TYPE X ALPHA-1 ASSAY

(71) Applicant: Nordic Bioscience A/S, Herlev (DK)

(72) Inventors: Yi He, Virum (DK); Anne-Cecilie Bay-Jensen, Copenhagen (DK); Morten Karsdal, Copenhagen (DK)

(73) Assignee: Nordic Bioscience A/S, Herlev (DK)

( * ) Notice: Subject to any disclaimer, the term of this patent is extended or adjusted under 35 U.S.C. 154(b) by 783 days.

(21) Appl. No.: 17/584,517

(22) Filed: Jan. 26, 2022

(65) Prior Publication Data

US 2022/0146528 A1 May 12, 2022

Related U.S. Application Data

(63) Continuation-in-part of application No. 16/634,158, filed as application No. PCT/EP2018/070430 on Jul. 27, 2018, now abandoned.

(30) Foreign Application Priority Data

Jul. 27, 2017 (GB) ..................................... 1712071

(51) Int. Cl.
*G01N 33/68* (2006.01)
*C07K 16/18* (2006.01)
*C12N 5/16* (2006.01)
*G01N 33/577* (2006.01)

(52) U.S. Cl.
CPC ......... *G01N 33/6887* (2013.01); *C07K 16/18* (2013.01); *C12N 5/16* (2013.01); *G01N 33/577* (2013.01); *C07K 2317/34* (2013.01); *G01N 2333/78* (2013.01); *G01N 2470/10* (2021.08); *G01N 2800/105* (2013.01)

(58) Field of Classification Search
None
See application file for complete search history.

(56) References Cited

U.S. PATENT DOCUMENTS

2016/0123993 A1* 5/2016 Jensen ................. G01N 33/564
435/7.5

OTHER PUBLICATIONS

Sole et al. (PLOS One 2014 9:e106748) (Year: 2014).*
Pincus et al. (Clin. Exp. Rheumatol. 2019 37:S7-S17 (Year: 2019).*

* cited by examiner

*Primary Examiner* — Changhwa J Cheu
(74) *Attorney, Agent, or Firm* — Benjamin Aaron Adler

(57) ABSTRACT

Provided herein is an antibody specifically reactive with an N-terminus neo-epitope of collagen type X alpha 1 in the amino acid sequence $H_2N$-GIATKGLNGP, and its use in an immunoassay for evaluating a disease associated with collagen type X alpha 1, such as osteoarthritis.

13 Claims, 5 Drawing Sheets

Specification includes a Sequence Listing.

SEQUENCE LISTING

```
<160> NUMBER OF SEQ ID NOS: 24

<210> SEQ ID NO 1
<211> LENGTH: 10
<212> TYPE: PRT
<213> ORGANISM: Homo sapiens
<220> FEATURE:
<223> OTHER INFORMATION: N-terminus neo-epitope biomarker of collagen
      type X alpha 1

<400> SEQUENCE: 1

Gly Ile Ala Thr Lys Gly Leu Asn Gly Pro
1               5                   10

<210> SEQ ID NO 2
<211> LENGTH: 6
<212> TYPE: PRT
<213> ORGANISM: Homo sapiens
<220> FEATURE:
<223> OTHER INFORMATION: N-terminus neo-epitope biomarker of collagen
      type X alpha 1

<400> SEQUENCE: 2

Gly Ile Ala Thr Lys Gly
1               5

<210> SEQ ID NO 3
<211> LENGTH: 11
<212> TYPE: PRT
<213> ORGANISM: Artificial Sequence
<220> FEATURE:
<223> OTHER INFORMATION: N-terminus elongated peptide

<400> SEQUENCE: 3

Ala Gly Ile Ala Thr Lys Gly Leu Asn Gly Pro
1               5                   10

<210> SEQ ID NO 4
<211> LENGTH: 9
<212> TYPE: PRT
```

```
<213> ORGANISM: Artificial Sequence
<220> FEATURE:
<223> OTHER INFORMATION: N-terminus truncated peptide

<400> SEQUENCE: 4

Ile Ala Thr Lys Gly Leu Asn Gly Pro
1               5

<210> SEQ ID NO 5
<211> LENGTH: 10
<212> TYPE: PRT
<213> ORGANISM: Artificial Sequence
<220> FEATURE:
<223> OTHER INFORMATION: Biotinylated peptide
<220> FEATURE:
<221> NAME/KEY: SITE
<222> LOCATION: 10
<223> OTHER INFORMATION: Biotin with optional linker between biotin and
      peptide

<400> SEQUENCE: 5

Gly Ile Ala Thr Lys Gly Leu Asn Gly Pro
1               5                   10

<210> SEQ ID NO 6
<211> LENGTH: 13
<212> TYPE: PRT
<213> ORGANISM: Artificial Sequence
<220> FEATURE:
<223> OTHER INFORMATION: Immunogenic peptide
<220> FEATURE:
<221> NAME/KEY: SITE
<222> LOCATION: 13
<223> OTHER INFORMATION: Keyhole limpet hemocyanin

<400> SEQUENCE: 6

Gly Ile Ala Thr Lys Gly Leu Asn Gly Pro Gly Gly Cys
1               5                   10

<210> SEQ ID NO 7
<211> LENGTH: 16
<212> TYPE: PRT
<213> ORGANISM: Artificial Sequence
<220> FEATURE:
<223> OTHER INFORMATION: Peptide fragment identified by mass
      spectrometry

<400> SEQUENCE: 7

Pro Gly Ser Lys Gly Asp Pro Gly Ser Pro Gly Pro Pro Gly Pro Ala
1               5                   10                  15

<210> SEQ ID NO 8
<211> LENGTH: 14
<212> TYPE: PRT
<213> ORGANISM: Artificial Sequence
<220> FEATURE:
<223> OTHER INFORMATION: Peptide fragment identified by mass
      spectrometry

<400> SEQUENCE: 8

Ser Lys Gly Asp Pro Gly Ser Pro Gly Pro Pro Gly Pro Ala
1               5                   10

<210> SEQ ID NO 9
<211> LENGTH: 10
<212> TYPE: PRT
<213> ORGANISM: Rattus norvegicus
<220> FEATURE:
<223> OTHER INFORMATION: Rat alignment sequence to SEQ ID NO: 1
```

```
<400> SEQUENCE: 9

Gly Ile Val Thr Lys Gly Leu Asn Gly Pro
1               5                   10

<210> SEQ ID NO 10
<211> LENGTH: 10
<212> TYPE: PRT
<213> ORGANISM: Mus musculus
<220> FEATURE:
<223> OTHER INFORMATION: Mouse alignment sequence to SEQ ID NO: 1

<400> SEQUENCE: 10

Gly Ile Ala Thr Lys Gly Leu Asn Gly Pro
1               5                   10

<210> SEQ ID NO 11
<211> LENGTH: 10
<212> TYPE: PRT
<213> ORGANISM: Bos taurus
<220> FEATURE:
<223> OTHER INFORMATION: Bovine alignment sequence to SEQ ID NO: 1

<400> SEQUENCE: 11

Gly Ile Ala Val Lys Gly Leu Asn Gly Pro
1               5                   10

<210> SEQ ID NO 12
<211> LENGTH: 10
<212> TYPE: PRT
<213> ORGANISM: Canus lupus familiaris
<220> FEATURE:
<223> OTHER INFORMATION: Dog alignment sequence to SEQ ID NO: 1

<400> SEQUENCE: 12

Gly Val Ala Thr Lys Gly Leu Asn Gly Pro
1               5                   10

<210> SEQ ID NO 13
<211> LENGTH: 16
<212> TYPE: PRT
<213> ORGANISM: Artificial sequence
<220> FEATURE:
<223> OTHER INFORMATION: Collagen type X alpha 1 antibody light chain
      complementarity-determining region CDR-L1

<400> SEQUENCE: 13

Arg Ser Ser Gln Ser Leu Val His Asn Asn Gly Asn Thr Tyr Leu His
1               5                   10                  15

<210> SEQ ID NO 14
<211> LENGTH: 7
<212> TYPE: PRT
<213> ORGANISM: Artificial sequence
<220> FEATURE:
<223> OTHER INFORMATION: Collagen type X alpha 1 antibody light chain
      complementarity-determining region CDR-L2

<400> SEQUENCE: 14

Lys Val Ser Asn Arg Phe Ser
1               5

<210> SEQ ID NO 15
<211> LENGTH: 9
<212> TYPE: PRT
<213> ORGANISM: Artificial sequence
<220> FEATURE:
```

<223> OTHER INFORMATION: Collagen type X alpha 1 antibody light chain
complementarity-determining region CDR-L3

<400> SEQUENCE: 15

Ser Gln Ile Thr His Val Pro Trp Thr
1               5

<210> SEQ ID NO 16
<211> LENGTH: 5
<212> TYPE: PRT
<213> ORGANISM: Artificial sequence
<220> FEATURE:
<223> OTHER INFORMATION: Collagen type X alpha 1 antibody heavy chain
complementarity-determining region CDR-H1

<400> SEQUENCE: 16

Ser Gly Phe Trp Ser
1               5

<210> SEQ ID NO 17
<211> LENGTH: 16
<212> TYPE: PRT
<213> ORGANISM: Artificial sequence
<220> FEATURE:
<223> OTHER INFORMATION: Collagen type X alpha 1 antibody heavy chain
complementarity-determining region CDR-H2

<400> SEQUENCE: 17

Tyr Ile Lys Tyr Ser Gly Asp Thr Tyr Phe Asn Pro Ser Leu Lys Ser
1               5                   10                  15

<210> SEQ ID NO 18
<211> LENGTH: 79
<212> TYPE: PRT
<213> ORGANISM: Artificial sequence
<220> FEATURE:
<223> OTHER INFORMATION: Collagen type X alpha 1 antibody light chain
with complementarity-determining regions and framework
sequences

<400> SEQUENCE: 18

Arg Ser Ser Gln Ser Leu Val His Asn Asn Gly Asn Thr Tyr Leu His
1               5                   10                  15

Trp Tyr Leu Gln Met Pro Gly Gln Ser Pro Lys Leu Leu Ile Tyr Lys
                20                  25                  30

Val Ser Asn Arg Phe Ser Gly Val Pro Asp Arg Phe Ser Gly Ser Gly
            35                  40                  45

Ser Gly Thr Asp Phe Thr Leu Lys Ile Ser Arg Val Glu Ala Glu Asp
        50                  55                  60

Leu Gly Val Tyr Phe Cys Ser Gln Ile Thr His Val Pro Trp Thr
65                  70                  75

<210> SEQ ID NO 19
<211> LENGTH: 70
<212> TYPE: PRT
<213> ORGANISM: Artificial sequence
<220> FEATURE:
<223> OTHER INFORMATION: Collagen type X alpha 1 antibody heavy chain
with complementarity-determining regions and framework
sequences

<400> SEQUENCE: 19

Ser Gly Phe Trp Ser Trp Ile Arg Lys Phe Pro Gly Asn Lys Leu Glu
1               5                   10                  15

Phe Met Gly Tyr Ile Lys Tyr Ser Gly Asp Thr Tyr Phe Asn Pro Ser

```
                    20                  25                  30

Leu Lys Ser Arg Ile Ser Ile Thr Arg Asp Thr Ser Lys Asn Gln Tyr
            35                  40                  45

Tyr Leu Gln Leu Asn Ser Val Thr Pro Glu Asp Thr Ala Thr Tyr Tyr
        50                  55                  60

Cys Ser Asp Met Asp Tyr
65                  70

<210> SEQ ID NO 20
<211> LENGTH: 112
<212> TYPE: PRT
<213> ORGANISM: Artificial sequence
<220> FEATURE:
<223> OTHER INFORMATION: Collagen type X alpha 1 antibody light chain
      variable region sequence

<400> SEQUENCE: 20

Asp Val Val Met Thr Gln Thr Pro Arg Ser Leu Pro Val Ser Leu Gly
1               5                   10                  15

Asp Gln Ala Ser Ile Ser Cys Arg Ser Ser Gln Ser Leu Val His Asn
            20                  25                  30

Asn Gly Asn Thr Tyr Leu His Trp Tyr Leu Gln Met Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ile
                85                  90                  95

Thr His Val Pro Trp Thr Phe Gly Gly Gly Thr Lys Leu Glu Ile Lys
            100                 105                 110

<210> SEQ ID NO 21
<211> LENGTH: 111
<212> TYPE: PRT
<213> ORGANISM: Artificial sequence
<220> FEATURE:
<223> OTHER INFORMATION: Collagen type X alpha 1 antibody heavy chain
      variable region sequence

<400> SEQUENCE: 21

Glu Val Gln Leu Gln Glu Ser Gly Pro Ser Leu Val Lys Pro Ser Gln
1               5                   10                  15

Thr Leu Ser Leu Thr Cys Ser Val Thr Gly Asp Ser Ile Thr Ser Gly
            20                  25                  30

Phe Trp Ser Trp Ile Arg Lys Phe Pro Gly Asn Lys Leu Glu Phe Met
        35                  40                  45

Gly Tyr Ile Lys Tyr Ser Gly Asp Thr Tyr Phe Asn Pro Ser Leu Lys
    50                  55                  60

Ser Arg Ile Ser Ile Thr Arg Asp Thr Ser Lys Asn Gln Tyr Tyr Leu
65                  70                  75                  80

Gln Leu Asn Ser Val Thr Pro Glu Asp Thr Ala Thr Tyr Tyr Cys Ser
                85                  90                  95

Asp Met Asp Tyr Trp Gly Gln Gly Thr Ser Val Thr Val Ser Ser
            100                 105                 110

<210> SEQ ID NO 22
<211> LENGTH: 219
<212> TYPE: PRT
```

<213> ORGANISM: Artificial sequence
<220> FEATURE:
<223> OTHER INFORMATION: Collagen type X alpha 1 antibody light chain
      variable and constant regions sequence

<400> SEQUENCE: 22

Asp Val Val Met Thr Gln Thr Pro Arg Ser Leu Pro Val Ser Leu Gly
1               5                   10                  15

Asp Gln Ala Ser Ile Ser Cys Arg Ser Ser Gln Ser Leu Val His Asn
            20                  25                  30

Asn Gly Asn Thr Tyr Leu His Trp Tyr Leu Gln Met Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ile
                85                  90                  95

Thr His Val Pro Trp Thr Phe Gly Gly Gly Thr Lys Leu Glu Ile Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Ile Val Lys Ser Phe Asn Arg Asn Glu Cys
    210                 215

<210> SEQ ID NO 23
<211> LENGTH: 447
<212> TYPE: PRT
<213> ORGANISM: Artificial sequence
<220> FEATURE:
<223> OTHER INFORMATION: Collagen type X alpha 1 antibody heavy chain
      variable and constant regions sequence

<400> SEQUENCE: 23

Glu Val Gln Leu Gln Glu Ser Gly Pro Ser Leu Val Lys Pro Ser Gln
1               5                   10                  15

Thr Leu Ser Leu Thr Cys Ser Val Thr Gly Asp Ser Ile Thr Ser Gly
            20                  25                  30

Phe Trp Ser Trp Ile Arg Lys Phe Pro Gly Asn Lys Leu Glu Phe Met
        35                  40                  45

Gly Tyr Ile Lys Tyr Ser Gly Asp Thr Tyr Phe Asn Pro Ser Leu Lys
    50                  55                  60

Ser Arg Ile Ser Ile Thr Arg Asp Thr Ser Lys Asn Gln Tyr Tyr Leu
65                  70                  75                  80

Gln Leu Asn Ser Val Thr Pro Glu Asp Thr Ala Thr Tyr Tyr Cys Ser
                85                  90                  95

Asp Met Asp Tyr Trp Gly Gln Gly Thr Ser Val Thr Val Ser Ser Ala

```
                100             105             110
Lys Thr Thr Pro Pro Ser Val Tyr Pro Leu Ala Pro Gly Cys Gly Asp
        115             120             125

Thr Thr Gly Ser Ser Val Thr Leu Gly Cys Leu Val Lys Gly Tyr Phe
        130             135             140

Pro Glu Ser Val Thr Val Thr Trp Asn Ser Gly Ser Leu Ser Ser Ser
145             150             155             160

Val His Thr Phe Pro Ala Leu Leu Gln Ser Gly Leu Tyr Thr Met Ser
        165             170             175

Ser Ser Val Thr Val Pro Ser Ser Thr Trp Pro Ser Gln Thr Val Thr
        180             185             190

Cys Ser Val Ala His Pro Ala Ser Ser Thr Thr Val Asp Lys Lys Leu
        195             200             205

Glu Pro Ser Gly Pro Ile Ser Thr Ile Asn Pro Cys Pro Pro Cys Lys
        210             215             220

Glu Cys His Lys Cys Pro Ala Pro Asn Leu Glu Gly Gly Pro Ser Val
225             230             235             240

Phe Ile Phe Pro Pro Asn Ile Lys Asp Val Leu Met Ile Ser Leu Thr
        245             250             255

Pro Lys Val Thr Cys Val Val Val Asp Val Ser Glu Asp Asp Pro Asp
        260             265             270

Val Gln Ile Ser Trp Phe Val Asn Asn Val Glu Val His Thr Ala Gln
        275             280             285

Thr Gln Thr His Arg Glu Asp Tyr Asn Ser Thr Ile Arg Val Val Ser
        290             295             300

Thr Leu Pro Ile Gln His Gln Asp Trp Met Ser Gly Lys Glu Phe Lys
305             310             315             320

Cys Lys Val Asn Asn Lys Asp Leu Pro Ser Pro Ile Glu Arg Thr Ile
        325             330             335

Ser Lys Ile Lys Gly Leu Val Arg Ala Pro Gln Val Tyr Ile Leu Pro
        340             345             350

Pro Pro Ala Glu Gln Leu Ser Arg Lys Asp Val Ser Leu Thr Cys Leu
        355             360             365

Val Val Gly Phe Asn Pro Gly Asp Ile Ser Val Glu Trp Thr Ser Asn
        370             375             380

Gly His Thr Glu Glu Asn Tyr Lys Asp Thr Ala Pro Val Leu Asp Ser
385             390             395             400

Asp Gly Ser Tyr Phe Ile Tyr Ser Lys Leu Asn Met Lys Thr Ser Lys
        405             410             415

Trp Glu Lys Thr Asp Ser Phe Ser Cys Asn Val Arg His Glu Gly Leu
        420             425             430

Lys Asn Tyr Tyr Leu Lys Lys Thr Ile Ser Arg Ser Pro Gly Lys
        435             440             445

<210> SEQ ID NO 24
<211> LENGTH: 3
<212> TYPE: PRT
<213> ORGANISM: Artificial sequence
<220> FEATURE:
<223> OTHER INFORMATION: Collagen type X alpha 1 antibody heavy chain
      complementarity region CDR-H3

<400> SEQUENCE: 24

Met Asp Tyr
1
```

COLLAGEN TYPE X ALPHA-1 ASSAY

SEQUENCE LISTING

The ASCII text file named D7721SEQ.txt created on Jan. 24, 2022 and containing 14 kb of text is hereby incorporated-by-reference herein.

BACKGROUND OF THE INVENTION

Technical Field

The present invention relates to an antibody which specifically reacts with an N-terminus neo-epitope of collagen type X alpha 1, and its use in a method of immunoassay for detecting and quantifying collagen type X alpha 1.

Background Art

Osteoarthritis (OA) is a common joint disease which is characterized by cartilage damage and loss of joint function. The etiology of OA comprises multiple factors including aging, obesity, trauma and heredity (1). The pathogenesis of OA is poorly understood due to the heterogeneity and complexity of this disease.

Remarkably, some characteristics of OA resemble chondrocyte differentiation processes during skeletal development by endochondral ossification. In healthy articular cartilage, chondrocytes resist proliferation and terminal differentiation. By contrast, chondrocytes in diseased cartilage progressively proliferate and develop hypertrophy. Moreover, vascularization and focal calcification of joint cartilage are initiated (2-5). The molecular events regulating chondrocyte differentiation are still unknown, but chondrocyte hypertrophy-like changes in OA have attracted more attention for study (6-8).

Type X Collagen Alpha-1:

Collagen type X alpha-1 is non-fibrillar, but forms fine pericellular filaments in association with cartilage collagen. The molecule isolated from chondrocyte cultures or from cartilage is a homotrimer of 59 kDa Collagen type X alpha-1 chains, and there have been reports of a recombinant molecule of collagen type X of approximately 75 kDa (9). Collagen type X alpha-1 shares a similar domain structure with type VIII collagen: a central triple-helical (COL1) domain of 50 kDa is flanked by N-terminal (NC2) and C-terminal (NC1) non-triple-helical domains (10). In addition, both collagen types represent major components of hexagonal lattice structure, in which the collagen molecules link together by interactions involving the non-triple-helical end regions.

Collagen type X alpha-1 distribution is restricted to normal fetal hypertrophic cartilage in the growth zones of long bones, vertebrae and ribs, and in adult (>21 yr) thyroid cartilage, where it may provide a scaffold to prevent local collapse as the cartilage matrix is removed during endochondral ossification (11). It is also found in bone fracture callus, in osteoarthritic cartilage and in chondrogenic neoplasms, and may be involved in cartilage mineralization.

Osteoarthritis:

OA is generally considered to be a non-inflammatory condition of the synovial joints, predominantly knee and hips. Chondrocyte hypertrophy and cartilage calcification are key pathological events in OA. Elevated expression of network-forming type X collagen is believed to be a specific signal for chondrocyte hypertrophy (12-15) therefore type X collagen can be used as a detectable marker for said disease.

There are several proteins associated with hypertrophic chondrocytes, such as collagen type X, MMP13, osteopontin, osteocalcin (16), Indian Hedgehog (17), Runx2 (18), VEGF (19), HtrA1 (20) and Transglutaminase-2 (TG-2) (21). Collagen type X and MMP13 are among the most widely used as markers of hypertrophic chondrocytes. However, synthesis of MMP13 can be induced in chondrocytes by inflammation and mechanical stress (22-23). Therefore, collagen type X as a hypertrophic chondrocyte specific marker can indicate a phenotype alteration of chondrocytes.

Thus, a method which accurately quantifies the amount of collagen type X or its fragments in a biological sample may allow a better understanding of collagen type X pathologies or physiological processes affecting collagen type X turnover such as OA. Evidently there is a need for such a method.

SUMMARY OF THE INVENTION

The inventors have now found that cathepsin K cleaves collagen type X alpha 1 at the peptide link between $^{478}$A-$G^{479}$, resulting in the formation of the N-terminus neo-epitope biomarker $H_2N$-$^{479}$GIATKGLNGP (SEQ ID NO: 1). This neo-epitope biomarker of collagen type X alpha 1 has been shown to correlate well with osteoarthritis.

Thus, in a first aspect the present invention relates to an antibody, wherein said antibody specifically binds to an N-terminus neo-epitope of collagen type X alpha 1 comprised in the amino acid sequence $H_2N$-GIATKGLNGP (SEQ ID NO: 1).

Preferably, the antibody specifically binds to the N-terminus amino acid sequence $H_2N$-GIATKG (SEQ ID NO: 2).

Preferably, the antibody does not specifically recognise or bind an N-extended elongated version of said N-terminus amino acid sequence. In this regard "N-extended elongated version of said N-terminus amino acid sequence" means one or more amino acids extending beyond the N-terminus of the sequence $H_2N$-GIATKGLNGP (SEQ ID NO: 1). For example, if the N-terminal amino acid sequence $H_2N$-GIATKGLNGP (SEQ ID NO: 1) was elongated by an alanine residue then the corresponding "N-extended elongated version" would be $H_2N$-AGIATKGLNGP... (SEQ ID NO: 3). Similarly, it is preferable that the antibody does not specifically recognise or bind an N-truncated shortened version of said N-terminus amino acid sequence. In this regard "N-truncated shortened version of said N-terminus amino acid sequence" means one or more amino acids removed from the N-terminus of the sequence $H_2N$-GIATKGLNGP (SEQ ID NO: 1). For example, if the N-terminal amino acid sequence $H_2N$-GIATKGLNGP (SEQ ID NO: 1) was shortened by one amino acid residue then the corresponding "N-truncated shortened version" would be $H_2N$-IATKGLNGP... (SEQ ID NO: 4).

The antibody is preferably a monoclonal antibody or fragment thereof. The invention includes a cell line producing such a monoclonal antibody or fragment thereof.

It should be understood that the antibody of the present invention is an artificial product resulting from the selection of a particular antigenic sequence determined by computational means (e.g. BLAST analysis) and generated by an artificially induced immune response. It should be understood that said antibody is not a product that has been isolated from a source that occurs naturally in nature.

Preferably, said antibody is a monoclonal antibody or fragment thereof having specific binding affinity. Said monoclonal antibody or fragment thereof may preferably comprise one or more complementarity-determining regions (CDRs) selected from:

CDR-L1:
RSSQSLVHNNGNTYLH, (SEQ ID NO: 13)

CDR-L2:
KVSNRFS, (SEQ ID NO: 14)

CDR-L3:
SQITHVPWT, (SEQ ID NO: 15)

CDR-H1:
SGFWS, (SEQ ID NO: 16)

CDR-H2:
YIKYSGDTYFNPSLKS, (SEQ ID NO: 17)
and

CDR-H3:
MDY. (SEQ ID NO: 24)

Preferably the antibody or fragment thereof comprises at least 2, 3, 4, 5 or 6 of the above listed CDR sequences.

Preferably the monoclonal antibody or fragment thereof has a light chain variable region comprising the CDR sequences

CDR-L1:
RSSQSLVHNNGNTYLH, (SEQ ID NO: 13)

CDR-L2:
KVSNRFS, (SEQ ID NO: 14)
and

CDR-L3:
SQITHVPWT. (SEQ ID NO: 15)

Preferably the monoclonal antibody or fragment thereof has a light chain that comprises framework sequences between the CDRs, wherein said framework sequences are substantially identical or substantially similar to the framework sequences between the CDRs in the light chain sequence below (in which the CDRs are shown in bold and underlined, and the framework sequences are shown in italics)

(SEQ ID NO: 18)
RSSQSLVHNNGNTYLH_WYLQMPGQSPKLLI_YKVSNRFS_GVPDRFSGSGS GTDFTLKISRVEAEDLGVYFC_SQITHVPWT.

Preferably the monoclonal antibody or fragment thereof has a heavy chain variable region comprising the CDR sequences

CDR-H1:
SGFWS, (SEQ ID NO: 16)

CDR-H2:
YIKYSGDTYFNPSLKS, (SEQ ID. NO: 17)

and

CDR-H3:
MDY. (SEQ ID. NO: 24)

Preferably the monoclonal antibody or fragment thereof has a heavy chain that comprises framework sequences between the CDRs, wherein said framework sequences are substantially identical or substantially similar to the framework sequences between the CDRs in the light chain sequence below (in which the CDRs are shown in bold and underlined, and the framework sequences are shown in italics)

(SEQ ID. NO: 19)
SGFWS_WIRKFPGNKLEFMG_YIKYSGDTYFNPSLKS_RISITRDTSKNQYY LQLNSVTPEDTATYYCSD_MDY.

As used herein, the framework amino acid sequences between the CDRs of an antibody are substantially identical or substantially similar to the framework amino acid sequences between the CDRs of another antibody if they have at least 70%, 80%, 90% or at least 95% similarity or identity. The similar or identical amino acids may be contiguous or non-contiguous.

The framework sequences may contain one or more amino acid substitutions, insertions and/or deletions. Amino acid substitutions may be conservative, by which it is meant the substituted amino acid has similar chemical properties to the original amino acid. A skilled person would understand which amino acids share similar chemical properties. For example, the following groups of amino acids share similar chemical properties such as size, charge and polarity: Group 1 Ala, Ser, Thr, Pro, Gly; Group 2 Asp, Asn, Glu, Gln; Group 3 His, Arg, Lys; Group 4 Met, Leu, Ile, Val, Cys; Group 5 Phe Thy Trp.

A program such as the CLUSTAL program to can be used to compare amino acid sequences. This program compares amino acid sequences and finds the optimal alignment by inserting spaces in either sequence as appropriate. It is possible to calculate amino acid identity or similarity (identity plus conservation of amino acid type) for an optimal alignment. A program like BLASTx will align the longest stretch of similar sequences and assign a value to the fit. It is thus possible to obtain a comparison where several regions of similarity are found, each having a different score. Both types of analysis are contemplated in the present invention. Identity or similarity is preferably calculated over the entire length of the framework sequences.

In certain preferred embodiments, the monoclonal antibody or fragment thereof may comprise the light chain variable region sequence:

(SEQ ID. NO: 20)
_DVVMTQTPRSLPVSLGDQASISC_RSSQSLVHNNGNTYLH_WYLQMPGQSP KLLI_YKVSNRFS_GVPDRFSGSGSGTDFTLKISRVEAEDLGVYFC_SQITH VPWT_FGGGTKLEIK_ and/or the heavy chain variable region sequence:

(SEQ ID. NO: 21)
*EVQLQESGPSLVKPSQTLSLTCSVTGDSIT*SGFWS*WIRKFPGNKLEFMG*

YIKYSGDTYFNPSLKS*RISITRDTSKNQYYLQLNSVTPEDTATYYCSD*

MDY*WGQGTSVTVSS*
(CDRs bold; Framework sequences in italics).

In a second aspect the present invention relates to a method of immunoassay for detecting in a biological sample fragments of collagen type X alpha 1 comprising an N-terminus neo-epitope amino acid sequence $H_2N$-GIATKGLNGP (SEQ ID NO: 1), said method comprising contacting said biological sample comprising said N-terminus neo-epitope amino acid sequence $H_2N$-GIATKGLNGP (SEQ ID NO: 1) with an antibody as described above, and determining the amount of binding of said antibody.

Preferably, said method is quantitative.

Preferably, said method is used to detect and/or quantify the amount of fragments of collagen type X alpha 1 comprising the N-terminus neo-epitope amino acid sequence $H_2N$-GIATKGLNGP (SEQ ID NO: 1) in biofluid.

The biofluid may be a patient derived biofluid. The biofluid may be, but is not limited to, blood, urine, synovial fluid, serum, plasma, or amniotic fluid.

The method of immunoassay may be, but is not limited to, a competition assay or a sandwich assay. The method of immunoassay may be, but is not limited to, a radioimmunoassay or an enzyme-linked immunosorbent assay.

The method may further comprise correlating the quantity of fragments of collagen type X alpha 1 comprising said N-terminus neo-epitope amino acid sequence $H_2N$-GIATKGLNGP (SEQ ID NO: 1) determined by said method with standard disease samples of known disease severity to evaluate the severity of a disease associated with collagen type X alpha 1.

Alternatively, or in addition to, the method may further comprise comparing the quantity of said fragments of collagen type X alpha 1 comprising said N-terminus neo-epitope amino acid sequence $H_2N$-GIATKGLNGP (SEQ ID NO: 1) determined by said method with standard values associated with healthy subjects to evaluate the presence and/or severity of a disease associated with collagen type X alpha 1.

In that regard, said method may further comprise correlating the quantity of fragments of collagen type X alpha 1 comprising said N-terminus neo-epitope amino acid sequence $H_2N$-GIATKGLNGP (SEQ ID NO: 1) determined by said method with standard osteoarthritis samples of known severity.

Similarly, said method may further comprise correlating the quantity of fragments of collagen type X alpha 1 comprising said N-terminus neo-epitope amino acid sequence $H_2N$-GIATKGLNGP (SEQ ID NO: 1) determined by said method with standard osteoarthritis samples of known severity in subjects of known age and gender and/or standard values associated with healthy subjects to evaluate the presence and/or severity of osteoarthritis. In this regard the comparison of samples is preferably between patient derived samples, wherein the patients (from whom the samples are derived) are of the same gender and of similar age to the standard samples.

The method may further comprise quantifying the amount of fragments of collagen type X alpha 1 comprising said N-terminus neo-epitope amino acid sequence $H_2N$-GIATKGLNGP (SEQ ID NO: 1) in at least two samples obtained from a subject at a first time point and at at least one subsequent time point, wherein a change in the quantity of said fragments from the first time point to the at least one subsequent time point is indicative of a change in the status of a disease associated with collagen type X alpha 1 from the first time point to the at least one subsequent time point.

For example, when the disease associated with collagen type X alpha 1 is osteoarthritis, an increase in the quantity of fragments of collagen type X alpha 1 comprising said N-terminus neo-epitope amino acid sequence $H_2N$-GIATKGLNGP (SEQ ID NO: 1) from the first time point to the at least one subsequent time point is indicative of a deterioration in osteoarthritis in a subject from the first time point to the at least one subsequent time point. Similarly, a decrease in the quantity of fragments of collagen type X alpha 1 comprising said N-terminus neo-epitope amino acid sequence $H_2N$-GIATKGLNGP (SEQ ID NO: 1) from the first time point to the at least one subsequent time point is indicative of an improvement in osteoarthritis in a subject from the first time point to the at least one subsequent time point.

In a final aspect, the present invention relates to an assay kit for detecting fragments of collagen type X alpha 1 comprising the N-terminus neo-epitope amino acid sequence $H_2N$-GIATKGLNGP (SEQ ID NO: 1) in a biological sample, said kit comprising an antibody as described above and at least one of:
- a streptavidin coated 96 well plate,
- a biotinylated peptide $H_2N$-GIATKGLNGP-L-Biotin (SEQ ID NO: 5), wherein L is an optional linker,
- a secondary antibody for use in a sandwich immunoassay,
- a calibrator peptide comprising the sequence $H_2N$-GIATKGLNGP,
- an antibody biotinylation kit,
- an antibody HRP labeling kit,
- an antibody radiolabeling kit, or
- an assay visualization kit.

DESCRIPTION OF THE FIGURES

FIG. 2A: MMPs cleaved human cartilage. FIG. 2B: ADAMTSs cleaved human cartilage. FIG. 2C: Cathepsin K cleaved human cartilage. Data shown as mean±SD. There was no increased level of Col10/C in none of the tested MMPs or ADAMTSs solution compared to the one without adding proteases in the digestion buffer. Conversely, Cathepsin K yielded the largest amount indicating its ability of releasing the fragment carrying the neo-epitope of 479GIATKGLNGP.

FIG. 3A: normal mouse IgG. FIG. 3B: 11G8, anti-C terminus of type X collagen. FIG. 3C: 2F4, anti-479GIATKG. Type X collagen detected by 11G8 occurred in the extracellular matrix of chondrocytes in the deep zone, but it was absent from the region of calcified cartilage. Surprisingly, in FIG. 3C the intense staining of 479GIATKG was seen in the extracellular matrix of chondrocytes from all zones in cartilage. Scale bar=500 μM.

FIG. 4A: Plasma Col10neo levels in different K/L groups. There was a trend toward increased Col10neo levels with a greater K/L grade, but not reaching statistical significance. FIG. 4B: The distribution of subjects with a K/L 3-4 in plasma Col10neo level by tertile. The one-way ANOVA with post-hoc Tukey-Kramer test was used. Plasma Col10neo data were logarithmic transformed in all analyses. P value<0.05 was considered statistically significant.

DESCRIPTION OF THE INVENTION

Definitions

Figure 1:
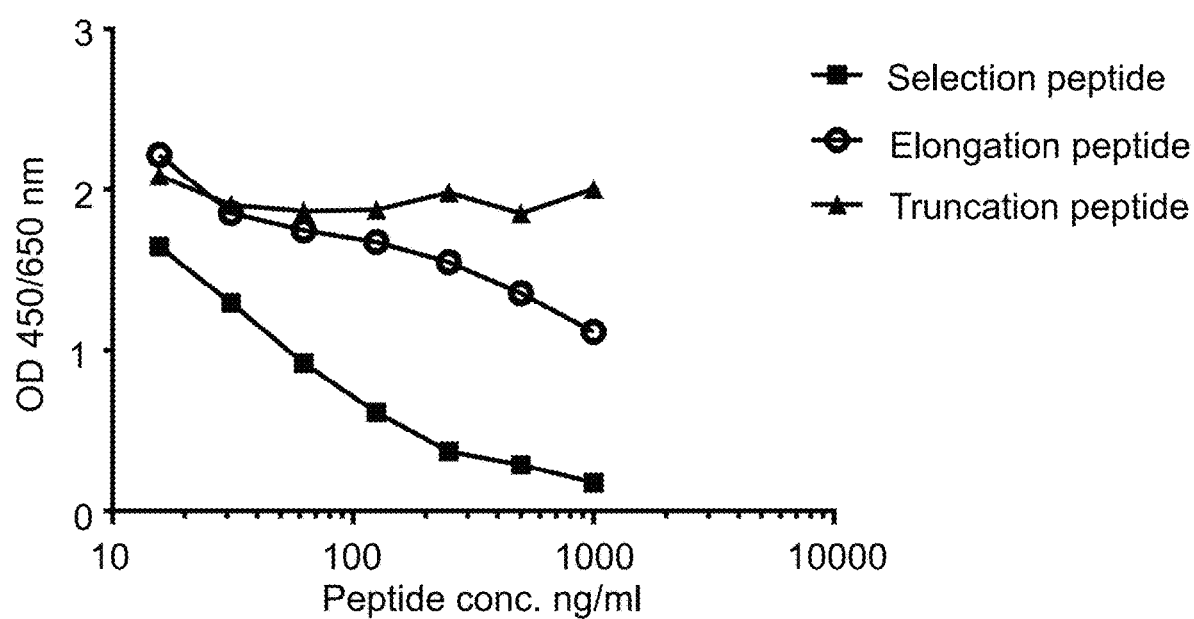
FIG. 1 shows the peptide-binding specificity of mAb. The reactivity of 2F4 toward a biotinylated synthetic peptide, GIATKGLNGP-k(Biotin) (SEQ ID NO: 5), was completely displaced by adding of 1000 ng/mL selection peptide. In contrast, a slight or no displacement was observed with elongation of selection peptide or truncation of selection peptide at the same concentration.

As used herein, the term "N-terminus" refers to the extremity of a polypeptide, i.e. at the N-terminal end of the polypeptide, and is not to be construed as meaning in the general direction thereof.

As used herein the term "N-terminus neo-epitope" refers to an N-terminus epitope formed by cleavage of a protein by a protease. For the instant invention this means an N-terminus epitope formed by cleavage of Collagen type X alpha-1 by cathepsin K.

As used herein, the term "fragments of collagen type X alpha 1 comprising an N-terminus neo-epitope amino acid sequence H$_2$N-GIATKGLNGP (SEQ ID NO: 1)" means peptide fragments of collagen type X alpha 1 wherein the N-terminus of the peptide fragment is the amino acid sequence H$_2$N-GIATKGLNGP . . . (SEQ ID NO: 1).

As used herein, the term, the term "competitive ELISA" refers to a competitive enzyme-linked immunosorbent assay and is a technique known to the person skilled in the art.

As used herein, the term "sandwich immunoassay" refers to the use of at least two antibodies for the detection of an antigen in a sample, and is a technique known to the person skilled in the art.

As used herein, the term "Col10neo" is used as shorthand to describe the herein disclosed specific assay for detecting and quantifying fragments of collagen type X alpha-1 comprising the N-terminus neo-epitope amino acid sequence H$_2$N-GIATKGLNGP (SEQ ID NO: 1).

EXAMPLES

The presently disclosed embodiments is described in the following Examples, which are set forth to aid in the understanding of the disclosure, and should not be construed to limit in any way the scope of the disclosure as defined in the claims which follow thereafter. The following examples are put forth so as to provide those of ordinary skill in the art with a complete disclosure and description of how to make and use the described embodiments, and are not intended to limit the scope of the present disclosure nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

In the following examples, the following materials and methods were employed.

Materials

Unless otherwise stated, all materials used for experiments were of high quality and ordered from Sigma-Aldrich (Copenhagen, Denmark) or VWR (Rodedovre, Denmark). The synthetic peptides used for monoclonal antibody production and assay development were purchased from GenScript (USA). MMP-2 catalytic domain (cat #G14MP02C), MMP-9 catalytic domain (cat #G04MP09C) and MMP-13 catalytic domain (cat #G04MP13C) were bought from Gitto Biotech (Florence, Italy). Cathepsin K (cat #219461), Cathepsin B (cat #219362) and Cathepsin S (cat #219343) and ADAMTS-4 (cat #CC1028) were from Merck Millipore (Darmstadt, Germany). ADAMTS-5 (cat #2198-AD-20) was purchased from R&D system (Minnesota, USA).

Selection of the Sequence for Immunization

The analysis for naturally occurring peptides in human urine from OA patients was carried out by LC-MS/MS. A significant amount of peptide fragments were identified in human OA urine. 17 peptide sequences were found to be unique to human type X collagen. Two among 17 sequences carrying the same free c-terminus located at amino acid (aa) position 478' (Accession No.: Q03692; Database: UniProt) were present in the diseased urine, indicating the cleavage occurring between the bond of $A^{478}$-$^{479}G$. The first 10 aa, $^{479}$GIATKGLNGP$^{488}$ (SEQ ID NO: 1), of the free N-terminal end generated by this cleavage was selected for immunization. The sequence alignment from different species was also analyzed using the Basic Local Alignment Search Tool (BLAST, see Table 1).

Monoclonal Antibody (mAb) Production

Six female Balb/C mice of 6-7 weeks of age were immunized subcutaneously with emulsified GIATKGLNGP-GGC-KLH (SEQ ID NO: 6) with Sigma Adjuvant System® (cat #56322, Sigma-Aldrich). 100 μg of emulsified KLH-conjugate with adjuvant was repeatedly injected into mouse every 3$^{rd}$ week until stable titer levels were obtained. At each bleeding, the serum antibody titer was measured against the biotinylated peptide, GIATKGLNGP-k(Biotin) (SEQ ID NO: 5) coated on streptavidin coated microplates (Roche Diagnostics, Germany). The mice with the highest antibody titer and best reactivity towards the selection peptide, GIATKGLNGP (SEQ ID NO: 1), was chosen for fusion (data not shown). The mouse selected was boosted intraperitoneally (i.p.) with 100 μg KLH-conjugate in 100 μL 0.9% sodium chloride solution three days before sacrificed for fusion. The fusion and antibody screening process was performed using standard techniques. Briefly, the spleen was surgically removed for isolation of splenocytes which was fused with murine myeloma cells, SP2/0-Ag14 (ATCC®CRL-1581™). Hybridoma cells were selected by using HAT (hypoxanthine Aminopterin Thymidine) medium. Supernatants were screened by an indirect ELISA, where the biotinylated peptide, GIATKGLNGP-k(Biotin) (SEQ ID NO: 5) was coated on streptavidin-precoated microplates. Standard limiting dilution process was carried out to select single cells. The isotype of antibody in supernatant was tested using the isotype determination kit, SBA Clonotyping System-HRP (5300-05, Southern Biotech). Single-cell derived hybridoma were transferred to 24-well plate to allow them for further growth, and eventually scale up from T25 to T175 flasks. The supernatants were collected and filtered with 0.2 μm filter before applying to a 1 mL HiTrap Protein G HP column (cat #17-0404-01, GE healthcare) for antibody purification.

The antibody generated was sequenced and the CDRs determined.

The sequence of the chains are as follows (CDRs in bold; Framework sequence in Italics; Constant region underlined):

```
Light chain: Amino acid sequence (238 aa)
(mouse Kappa isotype):
                                          (SEQ ID. NO: 22)
DVVMTQTPRSLPVSLGDQASISCRSSQSLVHNNGNTYLHWYLQMPGQSP

KLLIYKVSNRFSGVPDRFSGSGSGTDFTLKISRVEAEDLGVYFCSQITH

VPWTFGGGTKLEIKRADAAPTVSIFPPSSEQLTSGGASVVCFLNNFYPK

DINVKWKIDGSERQNGVLNSWTDQDSKDSTYSMSSTLTLTKDEYERHNS

YTCEATHKTSTSPIVKSFNRNEC,

CDR-L1:
                                          (SEQ ID. NO: 13)
RSSQSLVHNNGNTYLH,

CDR-L2:
                                          (SEQ ID. NO: 14)
KVSNRFS,
and

CDR-L3:
                                          (SEQ ID. NO: 15)
SQITHVPWT.

Heavy chain: Amino acid sequence (464 aa)
(Mouse IgH isotype)
                                          (SEQ ID. NO: 23)
EVQLQESGPSLVKPSQTLSLTCSVTGDSITSGFWSWIRKFPGNKLEFMG

YIKYSGDTYFNPSLKSRISITRDTSKNQYYLQLNSVTPEDTATYYCSDM

DYWGQGTSVTVSSAKTTPPSVYPLAPGCGDTTGSSVTLGCLVKGYFPES

VTVTWNSGSLSSSVHTFPALLQSGLYTMSSSVTVPSSTWPSQTVTCSVA

HPASSTTVDKKLEPSGPISTINPCPPCKECHKCPAPNLEGGPSVFIFPP

NIKDVLMISLTPKVTCVVVDVSEDDPDVQISWFVNNVEVHTAQTQTHRE

DYNSTIRVVSTLPIQHQDVVMSGKEFKCKVNNKDLPSPIERTISKIKGL

VRAPQVYILPPPAEQLSRKDVSLTCLVVGFNPGDISVEVVTSNGHTEEN

YKDTAPVLDSDGSYFIYSKLNMKTSKWEKTDSFSCNVRHEGLKNYYLKK

TISRSPGK,

CDR-H1:
                                          (SEQ ID. NO: 16)
SGFWS,

CDR-H2:
                                          (SEQ ID. NO: 17)
YIKYSGDTYFNPSLKS,
and

CDR-H3:
                                          (SEQ ID. NO: 24)
MDY.
```

$^{479}$GIATKG Specific Immuno-Assay (Col10neo)

A purified monoclonal antibody was first tested for peptide-binding specificity by three synthetic peptides, selection peptide (GIATKGLNGP; SEQ ID NO: 1), elongation of the selection peptide (AGIATKGLNGP; SEQ ID NO: 3) and truncation of the selection peptide (IATKGLNGP; SEQ ID NO: 4), and then used in a competitive immunoassay. After optimization with buffer, temperature, incubation time and concentrations for key reagents, the final protocol for detection of $^{479}$GIATKG (SEQ ID NO: 2) assay was developed as follows: a 96-well streptavidin pre-coated micro plate was coated with 1 ng/ml biotinylated peptide, GIATKGLNGP-k(Biotin) (SEQ ID NO: 5) dissolved in 50 mM PBS-BTB buffer (phosphate-buffered saline with bovine serum albumin and Tween-20, pH7.4) for 30 min at 20° C. Then, the plate was washed 5 times by standard wash buffer (20 mM Tris, 50 mM NaCl, pH 7.2). 20 μL of the peptide standards, kit controls or samples were added to appropriate wells, followed by 100 μL of 23 ng/ml monoclonal antibody in 50 mM PBS-BTB buffer containing 5% Osteocalcin EIA Puf-Liq (Roche diagnostics, Germany), and incubated overnight (20±1 hr) at 4° C. After 5 times wash, 100 μL of goat anti-mouse secondary antibody (115-035-003, Jackson ImmunoResearch) was added and incubated for 1 hr at 20° C. After this step, the plate was washed for 5 times with wash buffer. Finally, 100 μL 3,3',5,5'-tetramethylbenzidine (TMB) was added to each well and incubated for 15 min at 20° C. in the dark. The colorimetric reaction was stopped by adding 100 μL stopping solution (1% $H_2SO_4$) and measured at 450 nm with 650 nm as the reference.

The inter- and intra-plate variation were determined by 10 independent runs of quality control panel (three human sera and two peptide standard) in duplicate. The lower limit of detection (LLOD) was calculated as 3SD of the mean value of 21 zero standard. Multiple human serum or plasma samples were assayed neat, 2, 4, 6, 8, 16-fold in incubation buffer. Percent recovery was calculated as the measured concentration divided by the expected concentration corrected for dilution.

In Vitro Cleavage of Human Cartilage

Articular cartilage biopsies from osteoarthritis (OA) patients who underwent knee replacement surgery were obtained from Gentofte Hospital (Gentofte, Denmark). The retrieval of the specimens complied with international ethical guidelines for handling human samples and patient information. All participants signed an informed consent and the study was approved by Danish authority. To identify the enzymes responsible for the cleavage of the $A^{478}$-$^{479}G$ bond, cartilage was cleaved by numerous proteases including matrix metalloproteases (MMP2, MMP9 and MMP13), Cathepsins (CatK, CatB and CatS), and A disintegrin and metalloprotease domains with thrombospondins motifs (ADAMTS-4 and ADAMTS-5). 30 mg of snap-frozen and crushed cartilage with 1 μg each enzyme were placed in a 0.5 ml Eppendorf with 250 μL digestion buffer (digestion buffer for MMPs: 100 mM Tris, 100 mM NaCl, 10 mM $CaCl_2$ and 2 mM zinc acetate, pH 8.0; digestion buffer for ADAMTSs: 50 mM Tris, 100 mM NaCl and 10 mM $CaCL_2$, pH 7.5; digestion buffer for Cathepsins: 25 mM $NA_2HPO_4$, 150 mM NaCl, 2 mM EDTA, 2 mM DTT, pH 6.5). The digestion was carried out on one day in 2 replicates. 5 mM EDTA (broad-spectrum inhibitor for MMPs and ADAMTSs) and 5 mM E64 (broad-spectrum inhibitor for Cathepsins) were added to stop the reaction. All supernatants were stored at −80° C. prior to use.

Immunohistochemistry (IHC)

Cartilage with bone specimens for IHC were from the study in collaboration with Frederikshavn Hospital (Denmark) approved by Danish authority (N-20110031). All participants signed an informed consent. The specimens isolated from OA patients who underwent knee replacement surgery were fixed and decalcified, and then embedded in paraffin. 5 μm-thick cartilage sections were melt at 60° C. for 1 hr and deparrifined and hydrated, followed by antigen retrieval using Pronase E (cat #10165921001, Roche) at 37° C. for 10 min. The sections were treated by 0.5% casein in Tris Buffered Saline (TBS) for 30 min at room temperature to block unspecific binding. Immunostaining was performed by antibody NB117-2F4 developed in this study and previously developed antibody NB509-11G8. Immunoreactivity was visualized with peroxidase labeled anti-Mouse and diaminobenzidine (DAB, Dako, Denmark). Counterstaining was with Mayer's hematoxylin. The pictures were taken using an Olympus microscope BX60 equipped with an Olympus C5050 digital camera.

Study Participants

Plasma samples were retrieved from two studies, the C4Pain study approved by local ethics committee (N-20100094) (24) and the NYUHJD Progression study approved by local ethics committee (25-26). All participants provided informed consent prior to enrollment.

Briefly, the C4Pain is a cross-sectional study. It comprised 281 individuals with no joint degeneration to severe joint degeneration using the Kellgren/Lawrance (K/L) grading scale (K/L 0-4). The plasma samples from 253 enrollees were measured in the present study due to insufficient volume of other 28 samples.

The NYUHJD Progression study comprised 21 non-OA healthy controls (K/L1 and no pain in either knee), 146 OA patients (K/L 2) and 36 rheumatoid arthritis (RA) patients at baseline. 146 OA patients were further followed up for 24 months. The radiographic assessments were taken at baseline and 24 months and plasma were collected at baseline. Plasma samples from 20 non-OA healthy controls, 142 OA subjects and 34 RA subjects at baseline were available for measurement in the present study. However in the present study, we only investigated the level of Col10neo in different groups at baseline. Future studies will continue to move toward a more complete picture of Col10neo as a potential prognostic biomarker of radiographic progression in OA.

Statistics

Data were analyzed using GraphPad Prism 6 or MedCalc 16.8. For normality check, a Shaprio-Wilk test for all variables of interest was performed. Between group comparison for age, BMI and VAS score, the one-way ANOVA with post-hoc Tukey-Kramer test was used. Plasma Col10neo data were logarithmic transformed in all analyses. P value<0.05 was considered statistically significant. One asterisk (*) if p<0.05; two () if p<0.01; three (*) if p<0.001 and four (****) if p<0.0001.

Results

Peptide Selection

Sequence Alignment of the Selected Peptide Across Species 2 fragments sharing the same free C-terminal end, $^{463}$PGSKGDPGSPGPPGPA$^{478}$ (SEQ ID NO: 7) and $^{465}$SKGDPGSPGPPGPA$^{478}$ (SEQ ID NO: 8) were identified by mass spectrometry in urine of OA patients, indicating the presence of a cleavage site existing between A$^{478}$-$^{479}$G. A 10aa peptide from the free N-terminus generated by the cleavage, $^{479}$GIATKGLNGP (SEQ ID NO: 1), was chosen for immunization. The blast shows that among human proteins the sequence is unique to type X collagen alpha-1. Sequence similarity across species shows 100% identity between human and mouse, while a mismatched aa is contained in rat or bovine compared to human sequence.

TABLE 1

The sequence alignment of the chosen peptide across species

| Species | Sequence | Gene name | Acession | DataBase |
|---|---|---|---|---|
| Homo sapiens[1] | GIATKGLNGP | COL10A1 | Q03692 | UniProt |
| Rattus norvegicus[2] | GI_V_TKGLNGP | COL10A1 | A0A0G2K7A5 | UniProt |
| Mus Musculus[3] | GIATKGLNGP | COL10A1 | Q05306 | UniProt |
| Bos taurus[4] | GIA_V_KGLNGP | COL10A1 | P23206 | UniProt |
| Canis lupus familiaris[5] | G_V_ATKGLNGP | COL10A1 | Q2HNR1 | UniProt |

[1]Human (SEQ ID NO: 1); [2]Rat (SEQ ID NO: 9); [3]Mouse (SEQ ID NO: 10); [4]Bovine (SEQ ID NO: 11); [5]Dog (SEQ ID NO: 12)

Technical Performance of the Col10neo Assay

The monoclonal antibody 2F4 (isotype: IgG2b, κ) targeting $^{479}$GIATKG (SEQ ID NO: 2) was produced from hybridoma and purified by HiTrap Protein G affinity column (Cat #17-0404-01, GE Healthcare). In test for peptide-binding specificity, the reactivity of 2F4 toward a biotinylated synthetic peptide, GIATKGLNGP-k(Biotin) (SEQ ID NO: 5), was completely displaced by adding of 1000 ng/mL selection peptide. In contrast, a slight or no displacement was observed with elongation of the selection peptide or truncation of the selection peptide at the same concentration (FIG. 1). This indicated the developed antibody 2F4 was specific for the selection peptide.

The antibody 2F4 showing great specificity was therefore applied in a competitive ELISA assay, Col10neo. The technical performance of this assay is summarized and listed in table 2. The IC50 was 41.9 ng/mL. The intra-assay coefficient variation (CV %) was 3% and the inter-assay CV % was 11.8. The measurement range was 8-250 ng/mL. The linearity was good over a wide range of 4- to 32-fold dilution of serum and 8- to 64-fold dilution of EDTA-anticoagulated plasma.

TABLE 2

Summary of technical performance of Col10neo assay

| Assay specifications | Col10neo |
|---|---|
| IC50, ng/mL | 41.9 |
| Intra-assay, CV % | 3 |
| Inter-assay, CV % | 11.9 |

TABLE 2-continued

Summary of technical performance of Col10neo assay

| Assay specifications | Col10neo |
|---|---|
| Lower limit of detection, ng/mL | 0.127 |
| Measurement range, ng/mL | 8-250 |

Cathepsin K-Derived $^{479}$GIATKG

Figure 2A:
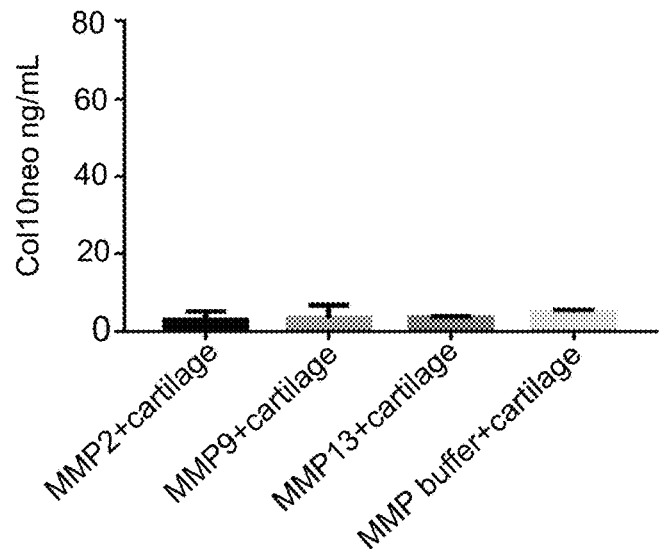
FIGS. 2A-2C show the in vitro cleavage of cartilage by enzymes.
Figure 2B:
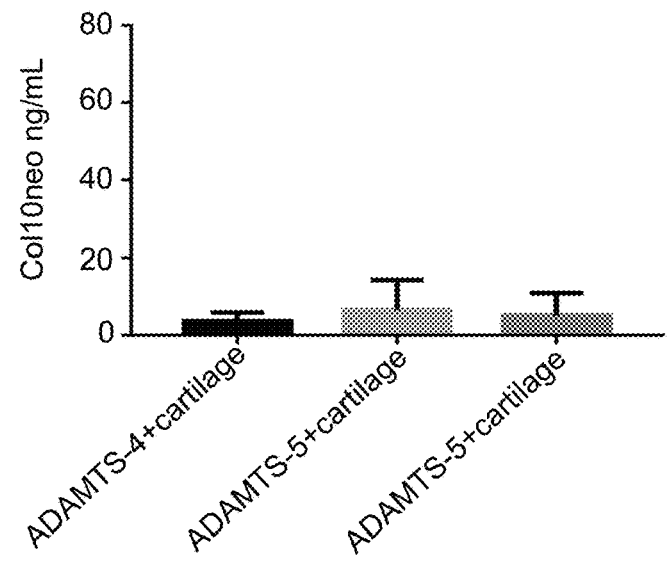
Figure 2C:
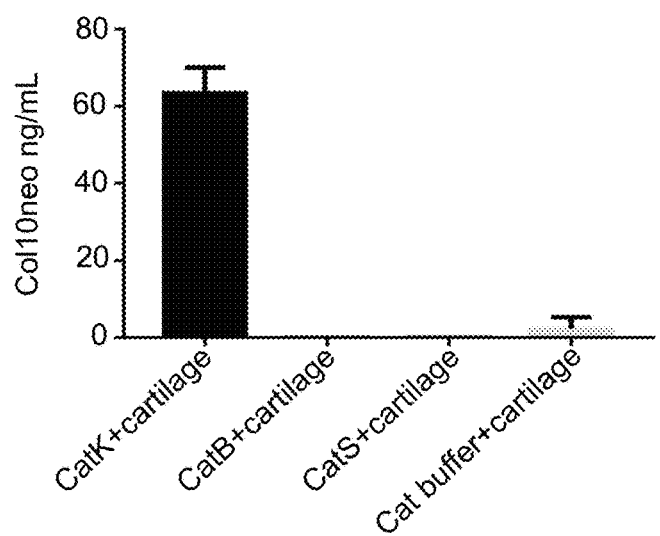

To investigate the responsible enzyme for cleaving $A^{478-479}G$ bond, several proteases were individually incubated with human cartilage. All proteases were at the same enzyme concentration and all incubations were performed for the same incubation time. The relative efficiency for each protease to generate the neo-epitope of $^{479}$GIATKGLNGP (SEQ ID NO: 1) was evaluated by applying to the Col10neo assay. There was no increased level of Col10neo in any of the tested MMPs or ADAMTSs solution compared to the one without adding proteases in the digestion buffer (FIGS. 2A-2B). Conversely, Cathepsin K yielded the largest amount indicating its ability of releasing the fragment carrying the neo-epitope of $^{479}$GIATKGLNGP (SEQ ID NO: 1) (FIG. 2C).

Immunolocalization of $^{479}$GIATKG in Cartilage

Figure 3A:
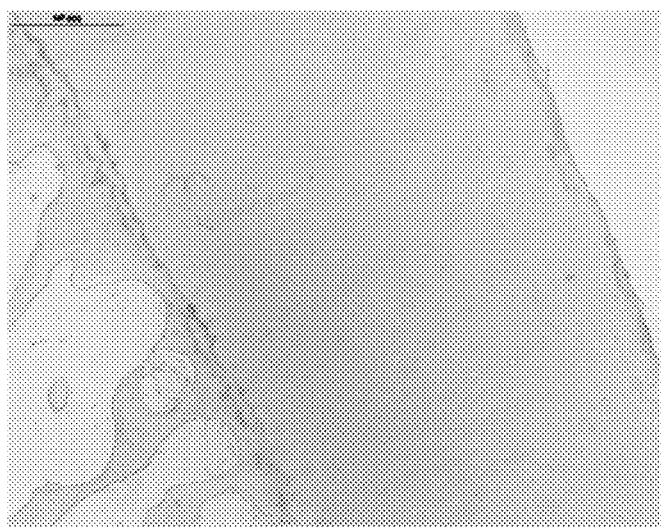
FIGS. 3A-3C show the immunolocalization of 479GIATKG in cartilage.
Figure 3B:
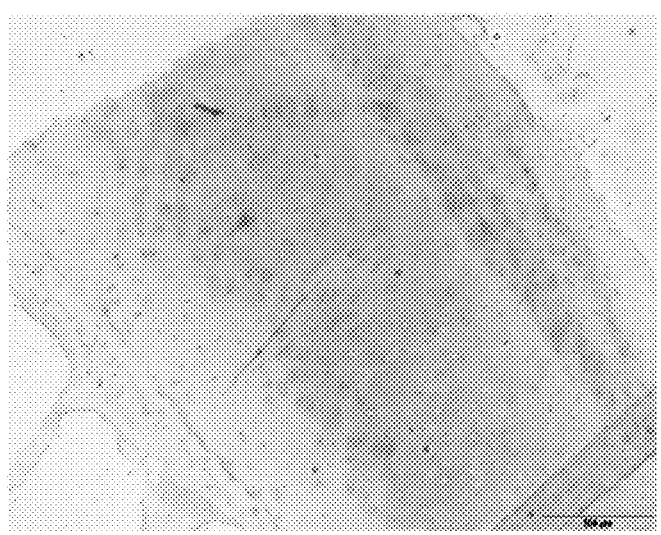
Figure 3C:
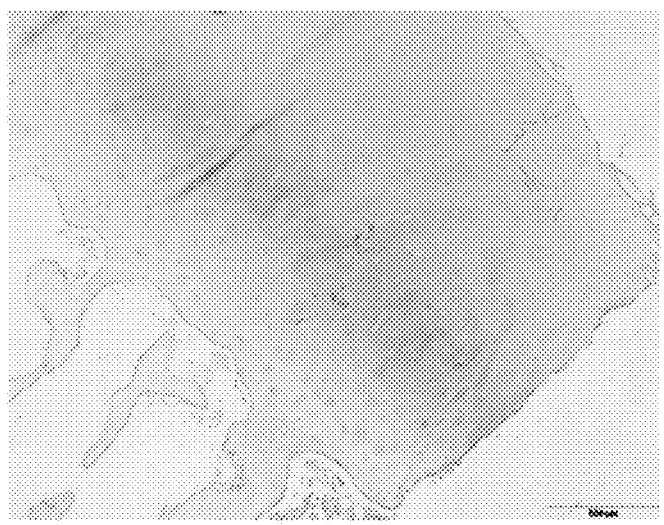

To further define the generation and distribution of $^{479}$GIATKG (SEQ ID NO: 2), consecutive sections of articular cartilage from a TKR (total knee replacement) patient were stained with anti-$^{479}$GIATKG (SEQ ID NO: 2) (2F4), normal mouse IgG (negative control) and anti-C terminus of type X collagen (11G8—disclosed in WO 2014/180992) as well. We did not observe any staining with normal mouse IgG (FIG. 3A). In line with previous studies, it was found that type X collagen detected by 11G8 occurred in the extracellular matrix of chondrocytes in the deep zone, but it was absent from the region of calcified cartilage (FIG. 3B). Surprisingly, the intense staining of $^{479}$GIATKG (SEQ ID NO: 2) was seen in the extracellular matrix of chondrocytes from all zones in cartilage (FIG. 3C). The staining of neo-epitope demonstrated that type X collagen released into the extracellular matrix had undergone further proteolytic processing.

Association Between K/L Grade and Plasma Col10neo Levels in the C4Pain Study

The 253 participants from the C4Pain study were categorized into 4 groups based on the K/L grade. The demographic characteristics of these 4 groups are summarized in Table 3.

TABLE 3

Demographics of subjects in the C4Pain study

| K/L grade | No. of men | No. of women | Total | VAS grade | Age, years | BMI, kg/m² |
|---|---|---|---|---|---|---|
| 0-1 | 23 | 27 | 50 | 37 ± 030 | 61.8 ± 08.5 | 26.4 ± 03.1 |
| 2 | 79 | 66 | 145 | 42 ± 029 | 64.6 ± 07.3 | 28.2 ± 03.8 |
| 3 | 17 | 19 | 36 | 56 ± 021 | 64.3 ± 07.1 | 29.3 ± 05.6 |
| 4 | 12 | 10 | 22 | 54 ± 024 | 67.8 ± 07.7$ | 29.5 ± 03.9 |

Except where indicated otherwise, values are the mean ± SD.
Vas grade = maximal pain intensity for the last 24 hour,
BMI = body mass index.
$P<0.05 compare to K/L0-1 group As the mean age of the participants was >60 years, the few participants with a K/L 0 or K/L of 1 were classified into the same group. 57% of the subjects involved in this study were with a K/L of 2 and assigned to group 2. There was no significant difference in gender distribution within each group. The mean age of K/L4 was significantly higher than K/L 0-1 group (p<0.005). There was a clear but not significant trend of increased BMI with an increase in K/L grade. The mean value of VAS score, defined as the maximal pain intensity for the last 24 hours, was not significantly different from each group.

Figure 4A:
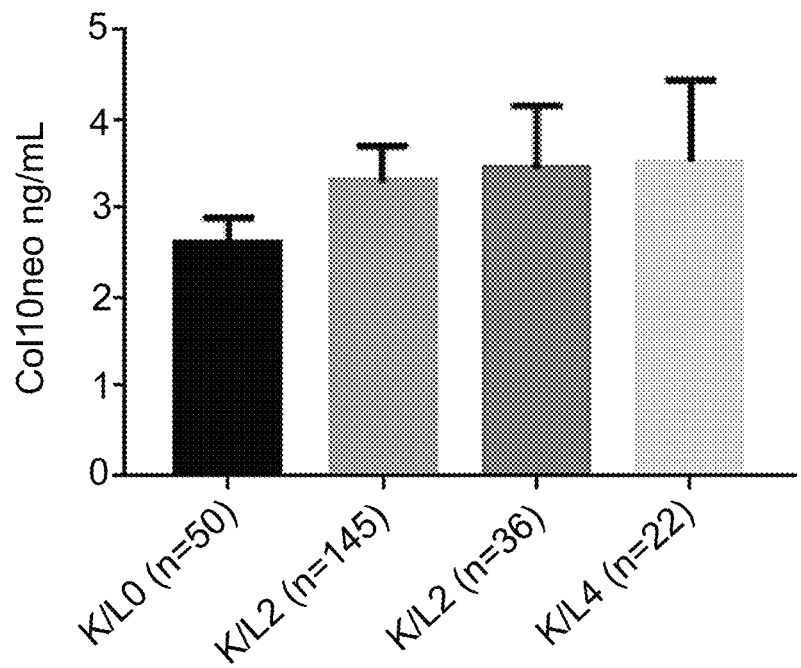
FIGS. 4A-4B show the association between KL grade and Col10neo level in the plasma of subjects in the C4Pain study. The data were shown as mean±95Cl %.
Figure 4B:
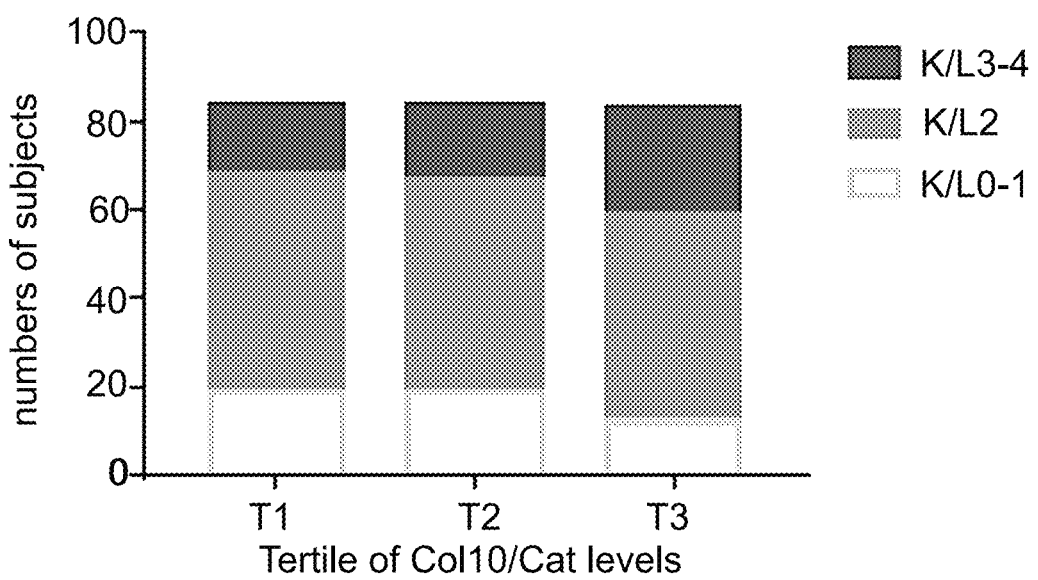

The mean±95Cl % concentrations of Col10neo for participants in 4 groups from KL 0-4 were 2.6 (2.316-2.884) µg/mL, 3.288 (2.885-3.691) µg/mL, 3.435 (2.729-4.141) µg/mL and 3.517 (2.599-4.435) µg/mL, respectively. There was a trend toward increased Col10neo levels with a greater K/L grade, but that did not reach statistical significance (FIG. 4A). The subjects were divided into tertiles based on the Col10neo levels and the distribution of K/L grade was compared (FIG. 4B). The number of subjects with a K/L 3-4 was greatest in those in the highest tertile of Col10neo.

Plasma Col10neo Levels in the NYUHJD Progression Study

The result from the C4Pain study caused us to investigate the potential of using Col10neo as a diagnostic biomarker in the NYUHJD Progression study which consists of non-OA healthy control, OA and RA. The percentage of female participants was higher in OA and RA groups than in the healthy control group. The mean age was significantly different in control and OA groups. However, the subjects were significantly younger in the RA group than in the OA group, since RA can occur at any age but has its peak between ages 30-55. There was a slight difference in BMI between healthy control and OA.

Figure 5:
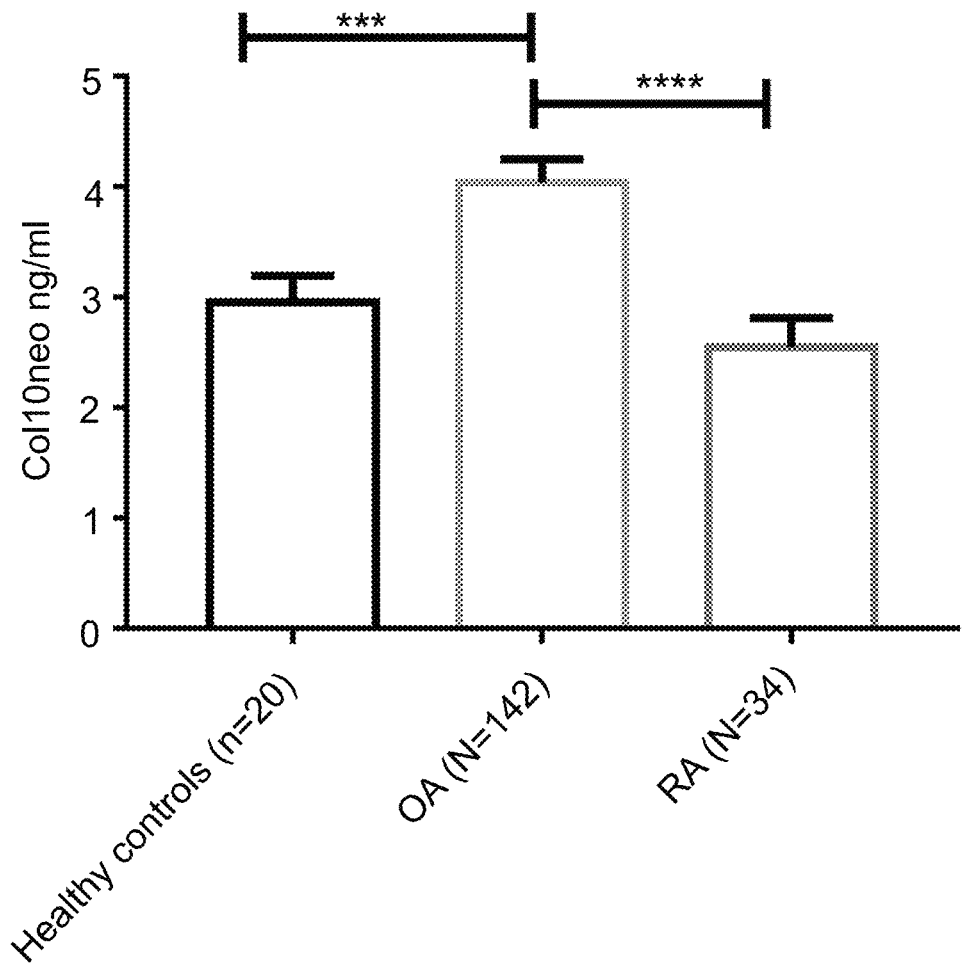
FIG. 5 shows the plasma Col10neo levels in the NYUHJD Progression study. The data were shown as mean±95Cl %. Plasma Col10neo was statistically higher in OA than healthy control (p=0.0002) or RA (p<0.0001). No significant difference in healthy control and RA was found. The one-way ANOVA with post-hoc Tukey-Kramer test was used. Plasma Col10/Cat data were logarithmic transformed in all analyses. P value<0.05 was considered statistically significant. One asterisk (*) if p<0.05; two () if p<0.01; three (*) if p<0.001 and four (****) if p<0.0001.

The plasma Col10neo (mean±95Cl %) in control, OA and RA was 2.953 (2.711-3.194) µg/mL, 4.04 (3.835-4.246) µg/mL and 2.548 (2.285-2.81) µg/mL, respectively (FIG. 5). Plasma Col10neo was statistically higher in OA than healthy control (p=0.0002) or RA (p<0.0001). No significant difference between the healthy control and RA was found. When the data was adjusted for age and gender, the level of Col10neo remained significantly increased in OA with respect to the control (p=0.003) or RA (p<0.0001) (Table 4).

Surprisingly, when adjusted for age and gender the difference between the control and Col10neo became significant for RA (p=0.0084; Table 4).

TABLE 5

ANCOVA analysis of plasma Col10neo levels adjusted for age and gender.

| Factors | | Mean difference | Std. Error | P $^a$ | 95% CI a |
|---|---|---|---|---|---|
| OA | healthy control | 0.1156 | 0.02913 | 0.0003 | 0.04527 to 0.1860 |
| | RA | 0.2200 | 0.02425 | <0.0001 | 0.1614 to 0.2786 |
| Healthy control | OA | −0.1156 | 0.02913 | 0.0003 | −0.1860 to −0.04527 |
| | RA | 0.1044 | 0.03446 | 0.0084 | −0.1860 to −0.04527 | a Bonferroni corrected

Concluding Remarks

It has been demonstrated that the herein disclosed col10neo assay is useful in the evaluation of OA. It is herein proposed that this usefulness may extend to evaluating other diseases associated with collagen type X alpha-1, such as ankylosing spondylitis.

In this specification, unless expressly otherwise indicated, the word 'or' is used in the sense of an operator that returns a true value when either or both of the stated conditions is met, as opposed to the operator 'exclusive or' which requires that only one of the conditions is met. The word 'comprising' is used in the sense of 'including' rather than in to mean 'consisting of'. All prior teachings acknowledged above are hereby incorporated by reference.

REFERENCES

1. Abhishek, A. and M. Doherty, Nat Rev Rheumatol, 7:96-104, 2011.
2. Kronenberg, H. M., Nature, 423:332-6, 2003.
3. Pfander, et al. Am J Pathol, 159:1777-83, 2001.
4. von der Mark, et al. Arthritis Rheum, 35:806-11, 1992.
5. Fuerst, et al. Arthritis Rheum, 60:2694-703, 2009.
6. Dreier, R. Arthritis Res Ther, 12:216, 2010.
7. Pitsillides, A. A. and F. Beier, Nat Rev Rheumatol, 7:654-63, 2011.
8. van der Kraan, P. M. and W. B. van den Berg, Osteoarthritis Cartilage, 20:223-32, 2012.
9. Frischholz, et al. J. Biol. Chem., 1998; 273:4547, 1998.
10. Yamaguchi, et al. J. Biol. Chem., 1989; 264:16022, 1989.
11. Olsen, B. J., and Ninomiya, Y., in: "Guidebook to the Extracellular Matrix and Adhesion Proteins", Kreis, T., and Vale, R. (eds.), Oxford University Press, Oxford, pp. 32-48, 1993.
12. Schmid, T. M., and Linsenmayer, T. F., in: "Structure and Function of Collagen Types", Mayne, R., and Burgeson, R. E. (eds.), Academic Press Inc., pp. 223-259, 1987.
13. Rucklidge, et al. Matrix Biol., 15:73, 1996.
14. Aigner, et al. Histochem. Cell Biol., 107:435, 1997.
15. Girkontaite, et al. Matrix Biol., 15:231, 1996.
16. Gerstenfeld, L. C. and F. D. Shapiro, J Cell Biochem, 62:1-9, 1996.
17. Wei, et al. Osteoarthritis Cartilage, 20:755-63, 2012.
18. Dong, et al. J Cell Physiol, 208:77-86, 2006.
19. Homer, et al. J Anat, 194:519-24, 1999.
20. Tsuchiya, et al. Bone, 37:323-36, 2005.
21. Huebner, et al. Osteoarthritis Cartilage, 17:1056-64, 2009.
22. Fitzgerald, et al. J Biol Chem, 283:6735-43, 2008.
23. Goldring, et al. Ann Rheum Dis, 67:75-82, 2008.
24. Arendt-Nielsen, et al. Arthritis Rheumatol (Hoboken, NJ). 66(12):3317-3326, 2014. doi:10.1002/art.38856.
25. Attur, M. et al. Osteoarthr Cartil. 2015; 23(11):1915-1924. doi:10.1016/j.joca.2015.08.006.
26. Attur, M. et al. Arthritis Rheumatol. 2015; 67(11):2905-2915. doi:10.1002/art.39279.

What is claimed is:

1. An antibody, wherein said antibody specifically reacts with an N-terminus neo-epitope of collagen type X alpha 1 comprised in the amino acid sequence H$_2$N-GIATKGLNGP (SEQ ID NO: 1); wherein the antibody comprises complementarity-determining regions (CDRs):
   CDR-L1: RSSQSLVHNNGNTYLH (SEQ ID NO: 13),
   CDR-L2: KVSNRFS (SEQ ID NO: 14),
   CDR-L3: SQITHVPWT (SEQ ID NO: 15),
   CDR-H1: SGFWS (SEQ ID NO: 16),
   CDR-H2: YIKYSGDTYFNPSLKS (SEQ ID NO: 17), and
   CDR-H3: MDY (SEQ ID NO: 24).

2. The antibody of claim 1, wherein said antibody specifically binds to the N-terminus amino acid sequence H$_2$N-GIATKG (SEQ ID NO: 2).

3. The antibody of claim 1, wherein the antibody does not specifically recognise or bind an N-extended elongated version of said N-terminus amino acid sequence or an N-truncated shortened version of said N-terminus amino acid sequence.

4. The antibody of claim 1, wherein said antibody is a monoclonal antibody or fragment thereof.

5. A cell line producing the monoclonal antibody of claim 4.

6. A method of immunoassay for detecting in a biological sample fragments of collagen type X alpha 1 comprising an N-terminus neo-epitope amino acid sequence H$_2$N-GIATKGLNGP (SEQ ID NO: 1), said method comprising contacting said biological sample comprising said N-terminus neo-epitope amino acid sequence H$_2$N-GIATKGLNGP (SEQ ID NO: 1) with the antibody of claim 1, and determining the amount of binding of said antibody.

7. The method of immunoassay of claim 6, wherein the detection is quantitative.

8. The method of immunoassay of claim 6, wherein said method is used to detect and/or quantify the amount of fragments of collagen type X alpha 1 comprising the N-terminus neo-epitope amino acid sequence H$_2$N-GIATKGLNGP (SEQ ID NO: 1) in a biofluid.

9. The method of immunoassay of claim 8, wherein said biofluid is a patient derived biofluid.

10. The method of immunoassay of claim 8, wherein said biofluid is blood, urine, synovial fluid, serum, or plasma.

11. The method of immunoassay of claim 6, wherein said method is a competition assay or a sandwich assay.

12. The method of immunoassay of claim 6, wherein said method is a radioimmunoassay or an enzyme-linked immunosorbent assay.

13. An assay kit for determining the quantity of fragments of collagen type X alpha 1 comprising the N-terminus neo-epitope amino acid sequence H$_2$N-GIATKGLNGP (SEQ ID NO: 1) in a biological sample, said kit comprising the antibody of claim 1 and at least one of:
   a streptavidin coated 96 well plate,
   a biotinylated peptide H$_2$N-GIATKGLNGP-L-Biotin (SEQ ID NO: 5), wherein L is an optional linker,
   a secondary antibody for use in a sandwich immunoassay,
   a calibrator peptide comprising the sequence H$_2$N-GIATKGLNGP (SEQ ID NO: 1),
   an antibody biotinylation kit,
   an antibody HRP labeling kit,
   an antibody radiolabeling kit; or
   an assay visualization kit.

* * * * *